United States Patent [19]

Guillemin et al.

[11] 4,288,322

[45] Sep. 8, 1981

[54] SAMPLE/STANDARD INJECTION HEAD FOR FLUID-PHASE CHROMATOGRAPH

[75] Inventors: Claude Guillemin, Paris; Christian Mayen, Creteil, both of France

[73] Assignee: Prolabo, Paris, France

[21] Appl. No.: 192,089

[22] Filed: Sep. 29, 1980

[30] Foreign Application Priority Data

Sep. 28, 1979 [FR] France ............................ 79 25520

[51] Int. Cl.³ ............................................ B01D 15/08
[52] U.S. Cl. ................................. 210/198.2; 210/291
[58] Field of Search ............... 210/198.2, 291; 55/197, 55/386; 73/23.1

[56] References Cited

U.S. PATENT DOCUMENTS

| | | | |
|---|---|---|---|
| 4,035,168 | 7/1977 | Jennings | 55/197 X |
| 4,124,358 | 11/1978 | Muller | 55/197 X |
| 4,168,235 | 9/1979 | Guilleman et al. | 210/198.2 |

Primary Examiner—John Adee
Attorney, Agent, or Firm—Burns, Doane, Swecker & Mathis

[57] ABSTRACT

An improved device/apparatus for sweeping and injecting a sample and at least one standard into the separation column of a fluid-phase chromatograph, including (i) means for securing same to the inlet of such separation column, (ii) a supply inlet for a stream of carrier medium and means for directing said stream to said separation column, (iii) dividing means in said device for dividing said stream into primary and secondary streams, (iv) distributing means for directing said primary stream to said separation column and distributing said primary stream over the inlet area of said column, (v) means for directing said secondary stream axially into said separation column inlet, and (vi) means for introducing a sample into said secondary stream, the improvement which comprises (vii) means for introducing at least one standard also into said secondary stream.

10 Claims, 7 Drawing Figures

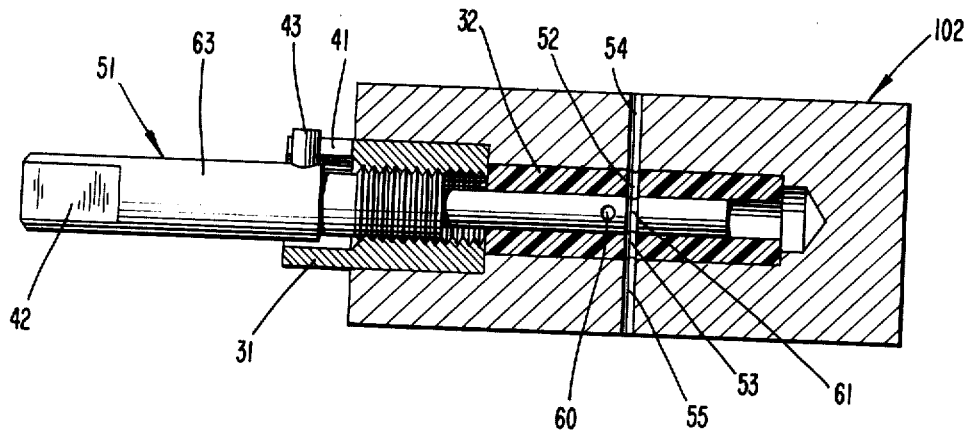
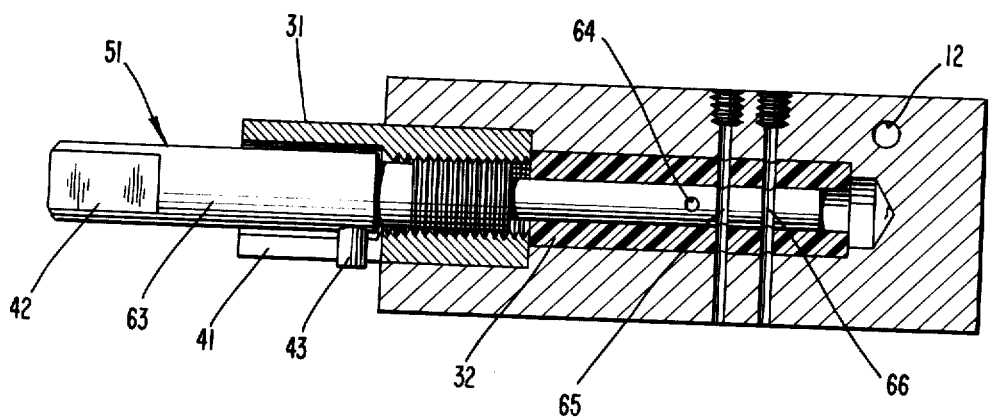
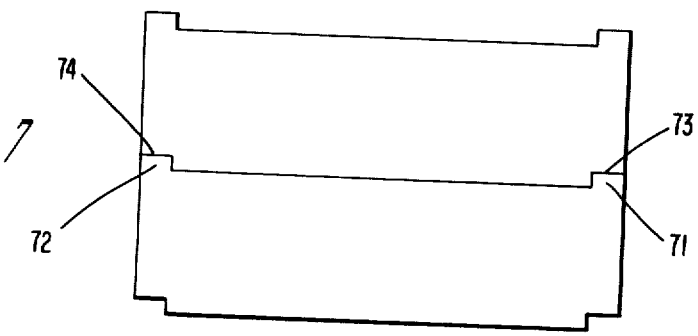

SAMPLE/STANDARD INJECTION HEAD FOR FLUID-PHASE CHROMATOGRAPH

BACKGROUND OF THE INVENTION

1. Field of the Invention

The present invention relates to means for the sweeping and injection of a sample and at least one standard for use in fluid-phase chromatography apparatus.

2. Description of the Prior Art

One particular analytical technique that is used in liquid phase chromatography includes comparing the chromatogram peaks of the components of the sample with the peak of at least one pure product designated a "standard". For this purpose, it is necessary to inject at least one standard after each sample, wherein the conditions of the injections must be such that there is no overlap between peak or peaks of the sample and the peaks of the standard. Especially in liquid-phase chromatography, satisfactory conditions of injection are difficult to establish. And even though the injection of the sample and of the standard or standards by inserting a syringe through a diaphragm affords good efficiency as regards column separation, this mode of injection has its disadvantages, because, on the one hand, the conditions of injection are difficult to reproduce from injection to injection, and, on the other hand, the linear velocity of the material injected (whether sample or standard) is often higher than the linear velocity of the carrier fluid, which results in turbulence at the inlet to the separation column.

The injection of the sample and the standard or standards may also be effected by means of valves. And while the valves provide a greater reproducibility of the conditions of injection, they reduce the efficiency of the column because of their design (the presence of dead space). Thus, in the case of two valves in series, in liquid-phase chromatography, with the upstream valve providing for injection of the standard, the efficiency of the column may be reduced up to 80% with respect to the standard.

SUMMARY OF THE INVENTION

Accordingly, a major object of the present invention is the provision of means for the injection of both a sample and at least one standard, with the conditions of injection remaining essentially identical for both the sample and for the standard or standards, and the same being perfectly reproducible from one analysis to another.

Another object of the present invention is the provision of means enabling separation column efficiency to be maintained high for both the sample and the standard(s).

Briefly, the present invention features an improvement of that device/apparatus disclosed and claimed in our earlier U.S. Pat. No. 4,168,235 hereby expressly incorporated by reference.

The device for the sweeping and injection of a sample into the separation column of a liquid-phase chromatograph which is the object of said U.S. Pat. No. 4,168,235 comprises means for securing same to the inlet of a separation column, a supply inlet for a stream of carrier liquid and means for directing said stream to said separation column. It also comprises means for the fractionating or dividing of the flow of the carrier liquid into a primary flow and a secondary flow, means for directing the primary flow to said separation column and distributing said primary flow over the entire inlet area of said column, means for directing the secondary flow axially into the center of the separation column inlet, and means for introducing a sample into said secondary flow.

More particularly, the subject means for the sweeping and injection of a sample and at least one standard to the separation column of a chromatograph which represents an improvement over that device featured in U.S. Pat. No. 4,168,235 comprises, in addition to said means for securing same to the inlet of a separation column, said supply inlet for a stream of carrier liquid and said means for directing said stream to said separation column, and conjunctively with (i) said dividing means in said device for dividing said stream into primary and secondary streams (ii) said distributing means for directing said primary stream to said separation column and distributing said primary stream over the entire inlet area of said column, (iii) said means directing said secondary stream axially into the center of said separation column inlet, and (iv) said means for introducing a sample into said secondary stream, the improvement comprising (v) means for introducing at least one standard into said secondary stream.

The expression "means for introducing a sample" or "means for introducing at least one standard" into the secondary stream are intended to denote both the means for supplying and for injecting the sample or the at least one standard into the secondary stream of the carrier liquid, such carrier liquid defining the moving phase of the chromatograph.

BRIEF DESCRIPTION OF THE DRAWINGS

The invention will be more clearly understood by reference to the annexed drawings which illustrate, by way of example only and which are not to scale, certain preferred embodiments of a device/apparatus according to the present invention.

FIG. 5 is a cross-sectional view along the plane V—V of the block 102 of FIG. 4;

FIG. 6 is a cross-sectional view along a plane perpendicular to the axis of the separation column, in another embodiment of the invention; and FIG. 7 is a front view of two blocks secured to each other in another embodiment of the invention.

DETAILED DESCRIPTION OF THE INVENTION

Figure 1:
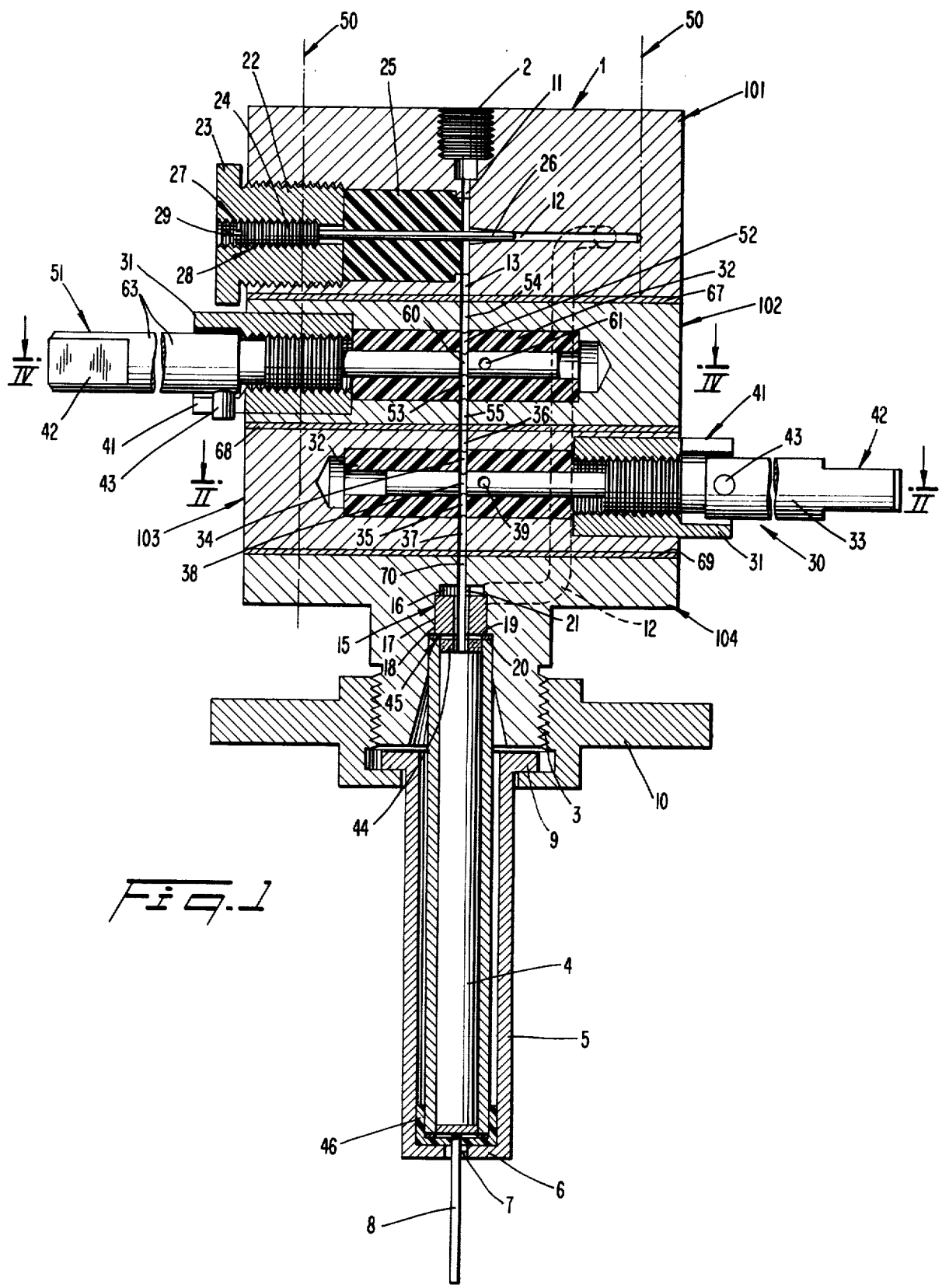
FIG. 1 is a cross-section along a plane containing the centerline of the separation column, of a sweeping and injection head secured to a separation column.

According to this invention, injection of a sample and of at least one standard consistent herewith connotes a single analytical sequence, comprising the injection of a sample into the separation column, followed by the injection of at least one standard. Such connotation, however, is not intended to exclude those specific embodiments whereby several analytical sequences are effected successively, i.e., whereby the injection of a first sample is followed by the injection of at least one standard; then the injection of a second sample is followed by the injection of at least one standard.

Preferably, the device according to the invention consists of an assemblage of blocks secured or fastened to each other by any appropriate means. Such a device comprises, from upstream to downstream in the direction of flow of the carrier fluid:

(a) a block containing an orifice for the supply of a feedstream of the carrier fluid and means for the fractioning or dividing of said feedstream of carrier fluid into a primary stream and a secondary stream;

(b) at least one block containing means for the introduction of at least one standard into said secondary flow;

(c) a block comprising means for the introduction of sample into said secondary stream;

(d) a block comprising:
  (di) means for the securing/mounting thereof to the block comprising the separation column;
  (dii) means for directing the primary stream to said separation column and distributing said primary stream over the entire inlet area of said column; and
  (diii) means for directing the secondary stream axially into the separation column inlet.

According to this particular embodiment of the invention, the block or blocks containing the means for the introduction of the standard or standards and the block containing means for introduction of a sample, may be quite similar.

In such embodiment of the invention, as illustrated in FIGS. 1 to 5 of the drawings, the device/apparatus 1 includes, from upstream to downstream in the downward direction of flow of the carrier fluid, four blocks, i.e.:

(i) a first block 101 comprising an orifice or supply inlet opening for the supply of the stream of the carrier fluid and means to fraction or divide the stream of said carrier fluid into a primary stream and a secondary stream.

(ii) a second block 102 comprising means for introduction of a standard into said secondary stream;

(iii) a third block 103 comprising means for introduction of a sample into said secondary stream; and (iv) a fourth block 104 comprising means for the securing/mounting thereof to the block housing the separation column, and means for directing the primary stream to said separation column and distributing said primary stream over the entire inlet area of said column.

The four blocks 101, 102, 103, 104 are more particularly described hereinbelow. According to the illustrated embodiment of the invention, the blocks are fastened together by means of screws 50, although a system of clamps or a system of springs could also be used.

The first block 101 contains an inlet port or orifice 2 for feeding a stream of carrier fluid; for this purpose, the orifice 2 may, for example, be threaded to permit ready connection with suitable coupling.

The inlet orifice 2 for the stream of carrier fluid is in communicating relationship with the feed conduit 11 for the carrier fluid.

In accordance with the embodiment illustrated in FIG. 1, the means for fractioning or dividing the stream of the carrier fluid into a primary flow and a secondary flow consists of the division of the feed conduit 11 of the carrier fluid into a primary conduit 12 and an upstream secondary conduit 13.

Advantageously, the means for the fractioning or dividing of the stream of carrier fluid comprises means to adjust the flow rate of the primary flow. This means of adjustment consists, for example, of a needle valve 22. The needle valve 22 comprises a hollow support 23, a needle 24 and a sealing device 25. The hollow support 23 is essentially cylindrical and is threaded both on its external and internal surfaces with threads; it may thus be attached within the block 101 by screwing into a threaded hole. The conically tapered tip 26 of the needle element 24 extends into the extremity of the principal conduit 12, which extremity is similarly of a conical configuration. The other end 27 of the needle element 24 is threaded at 28 whereby the needle 24 is attached to the interior of the hollow support 23 and a notch 29 is provided for adjusting the valve, for example, by means of a screwdriver, thus limiting the risk of an unintentional or accidental altering of its control setting.

The second block 102 comprises the means for the introduction of the standard into the secondary stream.

Figure 4:
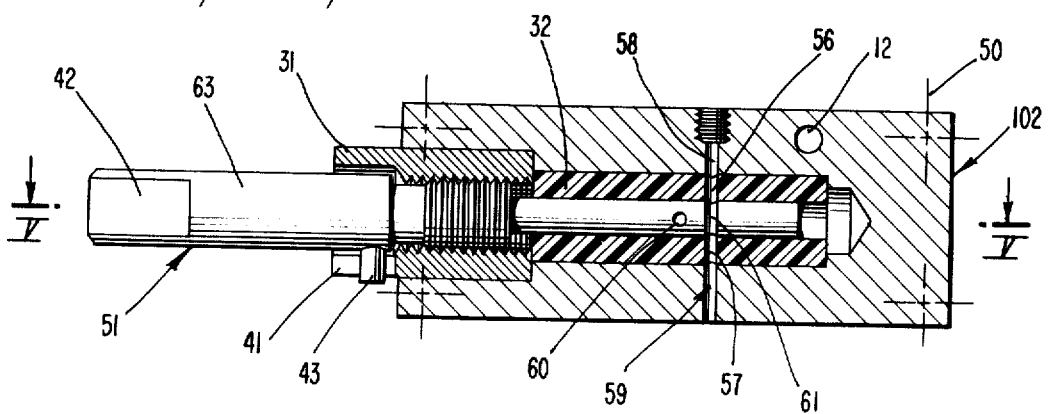
FIG. 4 is a cross-sectional view along the plane IV—IV of the block 102 of FIG. 1.

The means for introducing the standard into the secondary stream of the carrier fluid consist, in accordance with the embodiment of the invention illustrated in FIGS. 1, 4 and 5, of a valve 51 of piston-valve type.

The valve 51 consists of a valve support 31, a body member 32 and a piston 63.

The valve support 31, generally cylindrical in configuration, is set within an appropriately shaped cavity in the block 102, the support being threaded, at least in part. The wall of the support contains a cutout 41, bounded on the one hand by two planes containing the axis of the cylinder and defining an angle of approximately 90° (taking into account the diameter of the pin 43 described hereinafter), and, on the other hand, by a plane perpendicular to the axis of the cylinder.

The body member 32 of the valve 51 consists of a hollow cylinder placed into a cylindrical bore within the block 102; it comprises two sets of two diametrically opposed holes, longitudinally offset along the center line of the hollow body and offset angularly at an angle of approximately 90°. The first set of holes 52 and 53 is such that the holes communicate with the passages 54 and 55 of the block 102, the passage 54 communicating with the secondary upstream conduit 13 of the block 101. The second set of holes 56 and 57 communicate with channels 58 and 59 for the flushing introduction of the standard (FIG. 4).

Preferably, the body 32 is formed from polytetrafluoroethylene, a material which permits the piston 63 to slide easily within the hollow body 32, while at the same time providing a satisfactory tight sealing by mere contact between the external surface of the piston 63 and the internal surface of the body 32. Furthermore, polytetrafluoroethylene is highly inert with respect to chemical reagents.

The piston 63 within the body 32 has the general shape of an elongated cylinder; along its length and from the inside of the block 102 to the outside of said block it contains two zones, namely, the feed and standard injection zone toward the inside of the block 102 and the control zone toward the outside of the block 102.

The feed and injection zone comprises a channel 60 and a bore 61 for the standard. The channel 60 and the bore 61 are essentially diametrical and extend completely across the piston 63, from side to side. They are laterally offset along the longitudinal axis of the piston 63 and are also angularly offset by an angle of approximately 90°. When the piston 63 is in an axial and rotational position such as that shown in FIGS. 1 and 4, the channel 60 provides communication between the holes 52 and 53, which are in communication with the passages 54 and 55 and, upstream, with the secondary upstream conduit 13, while the bore 61 is then simultaneously in communicating relationship with the channels 58 and 59 for injection by flushing of the standard. The channel 58 is preferably threaded in the vicinity of the exterior of the block 102 to permit a coupling to be easily attached thereto. In another axial and rotational position of the piston 63, such as depicted in FIG. 5, the communicating relationship between the holes 54 and 53 is established by means of the bore 61, the channel 60 being closed.

The displacement of the piston 63 from the position depicted in FIGS. 1 and 4, to the position shown in FIG. 5, is a translation along the axis of the piston for a distance equal to the longitudinal offset or separation existing between the channel 60 and the bore 61 and a simultaneous rotation around the same axis through an angle equal to the angular offset existing between the channel 60 and the bore 61.

The control zone comprises both means for fastening the piston 63 to the support 31 and control means.

The means for securing the piston 63 to the support 31 is a threaded region which screws into the threaded internal surface of the support 31.

The control means consist, on the one hand, of a plate 42 located at the end of the piston 63 to allow for ready gripping of said end during operation of the piston 63 and, on the other hand, of a pin 43 which moves within the cutout 41 of the support 31, with the pin 43 stopping against the two planes containing the axis or centerline of the piston 63 at each position of the piston 63, either the channel 60 or the bore 61 being in communicating relationship with, on the one hand, the hole 52, the passage 54 and upstream the secondary upstream conduit 13, and, on the other hand, the hole 53 and the passage 55.

The principal conduit 12 continues in the block 102.

The third block 103 comprises the means for the introduction of the sample into the secondary stream.

Figure 2:
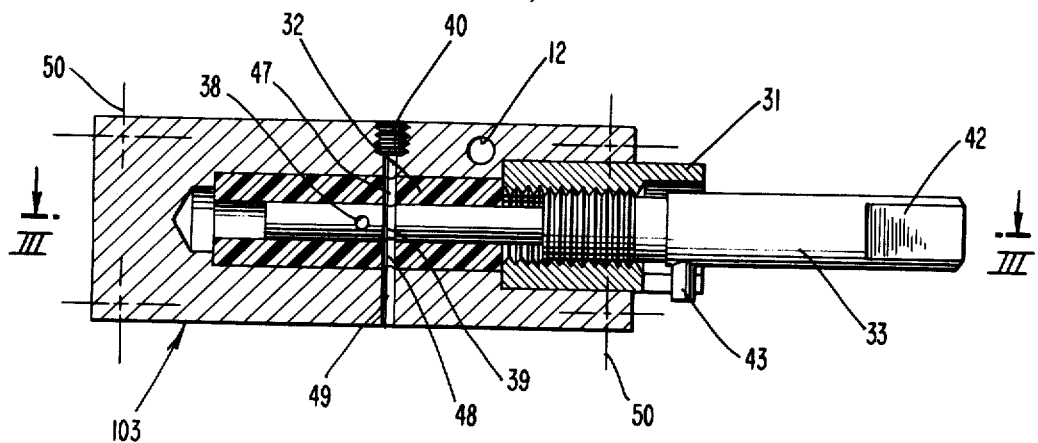
FIG. 2 is a cross-sectional view along the plane II—II of the block 103 of FIG. 1.
Figure 3:
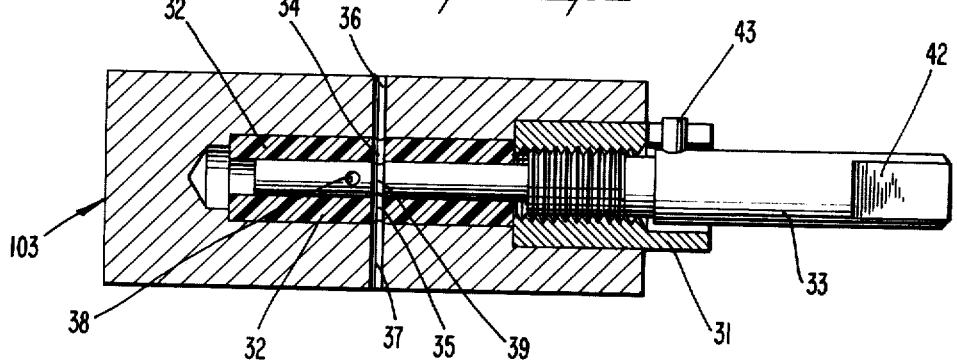
FIG. 3 is a cross-sectional view along the plane III—III of the block 103 of FIG. 2, during sample injection.

The means for the introduction of the sample to be analyzed into the secondary stream of the carrier fluid, according to the embodiment of the invention illustrated in FIGS. 1, 2 and 3, comprises a valve 30 of piston-valve type.

In the description of the valve 30, its component elements which do not perform a particular function, are designated by the same reference numerals heretofore employed for the elements constituting the valve 63.

The valve 30 consists of a valve support 31, a body element 32 and a piston 33.

The valve support 31 is similar to the valve support for the valve 51; compare the hereinabove description relating thereto.

The body element 32 of the valve 30 is similar to the body element of the valve 51; it again comprises two sets of diametrically opposed holes, longitudinally offset along the axis of the hollow body and offset angularly by an approximate angle of 90°. The first set of holes 34 and 35 is such that the holes are in communicating relationship with the channels 36 and 37 of the block 103, with the channel 36 in communicating relationship with the channel 55 of the block 102. Regarding the second set of holes 47 and 48, each is in communicating relationship with the channels 40 and 49 for the feedstream by flushing of the sample to be analyzed (FIG. 2).

The piston 33 is similar to the piston 63 associated with the valve 51.

The feed and injection zone comprises a channel 38 and a bore 39 for the sample to be analyzed. The channel 38 and the bore 39 are essentially diametrically opposed and traverse the piston 33 from side to side. They are essentially offset with respect to each other along the longitudinal axis of the piston 33 and angularly offset by an angle of approximately 90°. With the piston 33 in a position such as shown in FIGS. 1 and 2, the channel 38 insures a communicating relationship between the holes 34 and 35, the passages 36 and 37, and upstream the passage 55 and the bore 39 are simultaneously in communicating relationship with the channels 40 and 49 for the feed by flushing of the sample to be analyzed. The channel 40 is preferably threaded in the area of the outside of the block 103 in order to permit a coupling to be easily attached thereto. In another position of the piston 33, such as shown in FIG. 3, a communicating relationship between the holes 34 and 35 is established by means of the bore 39, with the passage 38 being closed off.

The displacement of the piston 33 in changing from the position illustrated in FIGS. 1 and 2 to the position shown in FIG. 3, was effected by means of translation movement along the axis of the piston for a distance equal to the longitudinal offset existing between the channel 38 and the bore 39, simultaneously with rotational movement about the same axis at an angle equal to the angular offset existing between the channel 38 and the bore 39.

The means for securing the piston 33 to the support 31 and the control zone are similar to those of the piston 63 of the valve 51.

The control means are also similar, with the pin 43 stopping against the two planes containing the axis or centerline of the piston 33, so that either the channel 38 or the bore 39 is in communicating relationship with the hole 34, the passage 36 and the passage 55, and likewise as regards the secondary upstream conduit 13.

The primary conduit 12 extends through the block 103.

The fourth block 104 comprises:

(i) means for the securing/mounting thereof to the separation column;

(ii) means for directing the primary stream to said separation column and distributing said primary stream over the entire inlet area of said column; and (iii) means for directing the secondary stream axially into the separation column inlet.

The means 3 for securing/mounting the separation column 4 advantageously comprises a screw threaded cylindrical zone or region.

The separation column may be secured to the device/apparatus according to the invention, for example, by means of a connection effected by the clamping of the column with a clamping ring or a clamping ring combined with a counter-clamp.

The separation column 4 may also be mounted, preferably as shown in FIG. 1, to the device/apparatus by exerting a compressive force essentially along the axis of the column 4. After the gaskets 45 and 46 are installed, the compressive force is exerted upon them by means of an essentially cylindrical column-holder tube 5, one end of which is sealed by a wall 6 provided with an aperture 7 through which passes an outlet tube 8 leading to the detector, and the other end of which is provided with an external, annular flange 9. A disc-shaped nut 10 engages the external, annular flange 9 of the column-holder tube 5 with the cylindrical threaded zone of the device according to the invention.

Such fastening means are described in our U.S. Pat. No. 4,162,977.

The means for supplying the primary feedstream, i.e., the primary conduit 12, opens into a chamber 15 provided with means for distributing the primary stream of the carrier liquid to the inlet 20 of the separation column 4. This chamber 15 consists of two zones, i.e., the supply or feed zone 16 and the distribution zone 17 provided with packing 18. The packing 18 preferably consists of a cylinder of a sintered metallic material. The feed zone 16 and the distribution zone 17 are generally cylindrical. The inlet end 20 of the separation column 4 is maintained in contact with the surface 19 of the packing 18 by the mounting means 3.

The packing 18 contributes to the uniform distribution of the primary stream of the carrier liquid at the inlet end 20 of the separation column 4; it also contributes to the smoothing of the flow by preventing the formation of turbulence eddies.

The means for supplying the secondary stream of the carrier liquid to the inlet end 20 of the separation column 4 consist of the secondary downstream conduit 70 in communicating relationship with the passage 37 of the block 103. The secondary downstream conduit 70, which advantageously is a capillary, continues as a hollow needle 21 which may be, for example, soldered to the block 104.

The hollow needle or tube 21 extends through the supply zone 16, the distribution zone 17 and emerges at the end of the distribution zone 17 and extends through a porous wall 44 located at the entrance inlet 20 of the separation column 4 at its center, i.e., axially with respect to the separation column 4. The length of the hollow needle or tube 21 is selected such that the needle will terminate just at the interface between the porous wall 44 and the packing material of the separation column 4.

In the device/apparatus according to the invention, during the sweeping of the separation column by the secondary stream, the latter successively passes from upstream to downstream through: the secondary upstream conduit 13, the passage 54, the hole 52, the channel 60, the hole 53, the passage 55, the passage 36, the hole 34, the channel 38, the hole 35, the passage 37, the secondary downstream conduit 70 and the hollow needle 21.

A gasket is preferably placed between two adjacent blocks; it is provided with the appropriate orifices for the passages of the primary flow and the secondary flow.

The device/apparatus shown in FIG. 1 thus comprises a gasket 67 placed between the first block 101 and the second block 102, a gasket 68 placed between the second block 102 and the third block 103, and a gasket 69 placed between the third block 103 and the fourth block 104.

Advantageously, the gaskets are made of polytetrafluoroethylene.

It should be understood that the invention is not limited to the embodiment specifically described in the present specification and that variations or improvements may be made without thereby exceeding the scope of the invention.

The device/apparatus according to the invention may be such that the means for the introduction of the sample and the means for the introduction of the standard consist of a single valve, for example, a single piston valve.

A block representing such a valve is shown, in cross-section, in FIG. 6. The feed and injection zone of the piston of the valve comprises, in addition to a passage 64 for the secondary flow, two bores 65 and 66. The bore 65 is intended for the sample and the bore 66 is intended for the standard. The bores 65 and 66 are essentially diametrical and pass through the injection zone from side to side; they are offset with respect to each other along the longitudinal axis of the piston and also angularly offset at an angle of approximately 90° with respect to the passage 64.

Such a device is formed by only three blocks, which are:

(i) a first and a third block similar to the first and the fourth block described hereinabove; and (ii) a second block comprising both the means for the introduction of the standard and of the sample into the secondary flow.

According to this embodiment of the invention, the second block comprises both a channel for the feeding of the sample by flushing and a channel for the feeding by flushing of the standard.

Another embodiment of the device/apparatus according to the invention features a block similar to the block shown in FIG. 6 as the means for the introduction of two standards in the secondary flow. The bores intended for the standards may have the same or different volumes.

Yet another embodiment of the device/apparatus according to the invention includes the feature wherein the feed and injection zone of the valve 30 and/or the valve 51 comprises several bores. These bores, in the same valve, may have identical or different volumes. According to this embodiment, two continuous bores are offset with respect to each other both longitudinally along the axis of the piston as well as angularly at an angle or approximately 90°. The injection of the two samples or standards is successively effected by the displacement of the piston by means of translational movement combined with rotational movement.

It is also possible, for example, to replace the piston valves 30 and 51 described hereinabove with slide valves. The slide of such valves may be provided with a channel and bore analogous to the channel and bore of the piston valves. The channel and bore are essentially cylindrical, have parallel axes and traverse the slide from side to side; they are slightly offset longitudinally. Thus, at one position of the slide, the channel connects with the secondary flow conduit and the bore connects with the feed channel of the sample to be analyzed or of the standard. By moving the slide by translation, the bore containing the sample or the standard is placed in communicating relationship with the secondary conduit and the secondary flow then sweeps the sample or the standard.

The piston valves may also be replaced with rotary valves wherein a rotatable disk could be provided with a channel and a bore. The channel and the bore are essentially symmetrical; have parallel axes, extend completely through the disk from side to side, are located at equal distances from the axis of rotation of the disk and are offset angularly. Rotation of the disk would bring the bore in communicating relationship with the secondary conduit and the secondary flow would sweep the sample or the standard.

Also without going beyond the scope of the invention, the piston valves may be replaced by barrel valves. These valves are similar to rotary valves, but the disk of such valves contains a plurality of bores. Using such valves, it is easy to effect repeated or multiple injections.

It too is within the ambit of the invention to fabricate the subject device/apparatus from blocks having face surfaces which are not flat as regards two adjacent blocks. In effect, one of the face surfaces may be comprised of at least two lateral edges corresponding to at least two grooves on the other face surface. FIG. 7 is an external front view of two such blocks consistent with this embodiment comprising two edges 71 and 72 and two grooves 73 and 74 in assembled state. This embodiment facilitates the positioning of the blocks during the assembly of the device/apparatus.

The scope of the invention is also not exceeded by the combination of the means for the introduction of the sample and/or the standard into the secondary flow with means for automatic control, such as, for example, a servomotor.

The operation of the subject device/apparatus will now be described, with particular reference to the embodiment shown in FIGS. 1 to 5.

After connecting the inlet orifice 2 to the feed supply of the carrier liquid (not shown) by means of appropriate tubing, the separation column 4 is installed in place and there maintained by a substantially axial compressive force, such as described hereinabove; the hollow needle or tube 21 extends through the porous wall 44 located at the inlet 20 of the separation column 4 and terminates just at the interface between the porous wall and the packing. The channel 40 is then connected to a source of the sample to be analyzed (not shown) and the channel 58 to a source of the standard (not shown). The head for the sweeping and injection into the separation column of a chromatograph is then ready for analysis and the flow of the carrier liquid is commenced.

With the piston 33 of the valve 30 being in the position shown in FIGS. 1 and 2, and the piston 63 of the valve 51 being in the position shown in FIGS. 1 and 4, the needle valve 22 is manipulated to adjust the rate of flow of the primary stream as a function of the conditions of the analysis to be effected; the primary stream then flows through the primary conduit 12 and is uniformly distributed by the packing 18 over the entire cross-section of the separation column 4, concentrically with respect to the hollow needle 21.

The secondary stream then successively flows through the upstream secondary conduit 13, the passage 54, the hole 52, the channel 60, the hole 53, the passage 55, the passage 36, the hole 34, the channel 38, the hole 35, the passage 37, the downstream secondary conduit 70 and the hollow needle 21. The secondary flow is thus fed axially to the inlet 20 of the separation column, just beneath the porous wall 44. Simultaneously, the sample to be analyzed has filled the bore 39 by flushing and the standard has filled the bore 61 by flushing.

The sample contained in the bore 39 is injected by reason of the combined rotational and translational movements, guided by the pin 43 which is moving in the cutout 41, of the piston 33 of the valve 30 such that the bore 39 is brought into communicating relationship with the holes 34 and 35, in place of the channel 38, as shown in FIG. 3. The secondary flow then sweeps the sample contained in the bore 39 and entrains it axially into the separation column 4.

When the peaks of the sample are being drawn or have been drawn by the recorder associated with the detector, the standard contained in the bore 61 is injected. For this purpose, by means of the combined rotational and translational movements guided by the pin 43 which moves in the circuit 41, the piston 63 of the valve 51 is displaced such as to bring the bore 61 in communicating relationship with the holes 52 and 53, in place of the passage 60, as shown in FIG. 5. The secondary flow then flushes the standard contained in the bore 61 and entrains it axially into the separation column 4.

The device/apparatus for the sweeping and injection of a sample and of at least one standard in the separation column of a chromatograph which is the object of the invention, has numerous advantages. Such a device makes it possible to achieve injection conditions of which are reproducible, for the sample and for the standard or standards, during the same analysis and from one analysis to the next. In fact, the speeds of injection of the sample and of the standard or standards are identical among themselves and from one analysis to the next and equal the speed of the secondary stream of carrier liquid. Furthermore, from the moment when the sample or the standard is injected, the flow conditions of the carrier liquid in the separation column do not vary. In particular, no change takes place in the rate of flow within the separation column, because prior to the injection and during the injection of the sample or of the standard, the carrier liquid traverses the separation column at the same speed.

In addition, such a device/apparatus is particularly advantageous for use upstream of a short separation column. In effect, when short separation columns are used, the loss of the pressure head of the carrier liquid upstream of the separation column is significant in relation to the loss of the pressure head induced within the separation column itself. It is therefore important that the loss of pressure upstream of the separation column should not vary over the course of the analysis and particularly that the device/apparatus according to the invention does not effect variations in the loss of pressure upstream of the separation column.

The device/apparatus according to the invention also exhibits the advantage of effecting the injections of the sample and of the standard or standards under conditions that are similar to ideal conditions of injection by syringe, as the sample to be analyzed and the standard or standards to be analyzed are injected into the separation column just beneath the porous wall by means of a capillary conduit, which increases the performance of the separation columns by virtue of the perfect centering of the injections at a constant level at the head of the column. Furthermore, since the primary flow of carrier liquid is distributed concentrically around the sample and the standard, radial diffusions of the latter are avoided.

Another advantage of the device/apparatus according to the invention is the increase in efficiency of the separation column with respect to the standard, which approaches the efficiency of the column for the sample.

The subject device/apparatus for the sweeping and injection of the sample and at least one standard consistent with the present invention may also be utilized to gaseous phase chromatography, wherein the carrier fluid is a gas (while in liquid-phase chromatography the carrier fluid is a liquid). The device/apparatus is preferably utilized to effect the sweeping and the injection of a sample and at least one standard in liquid-phase chromatography, however.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a device for sweeping and injecting a sample and at least one standard into the separation column of a fluid-phase chromatograph, including (i) means for securing same to the inlet of such separation column, (ii) a supply inlet for a stream of carrier medium and means for directing said stream to said separation column, (iii) dividing means in said device for dividing said stream into primary and secondary streams, (iv) distributing means for directing said primary stream to said separation column and distributing said primary stream over the entire inlet area of said column, (v) means for directing said secondary stream axially into said separation column inlet, and (vi) means for introducing a sample into said secondary stream, the improvement which comprises (vii) means for introducing at least one standard also into said secondary stream.

2. The device as defined by claim 1, wherein said dividing means include primary and secondary conduits communicating with said supply inlet.

3. The device as defined by claim 2, said means (vii) for introducing at least one standard into said secondary stream comprising a piston valve.

4. The device as defined by claim 2, said means (vi) and (vii) each comprising a single piston valve.

5. The device as defined by claim 2, said means (vii) for introducing at least one standard into said secondary stream comprising a rotary valve.

6. The device as defined by claim 2, said means (vii) for introducing at least one standard into said secondary stream comprising a barrel valve.

7. The device as defined by claim 2, the same comprising a serially, fixedly assembled array of block housing members including said means (i) to (vii).

8. The device as defined by claim 7, the same consecutively comprising (a) a first block including a supply inlet opening for the supply of the stream of the carrier fluid and means to divide the stream of said carrier fluid into a primary stream and a secondary stream, (b) a second block including means for introduction of a standard into said secondary stream, (c) a third block including means for introduction of a sample into said secondary stream, and (d) a fourth block including means for the securing/mounting thereof to the block housing the separation column, and means for directing the primary stream to said separation column and distributing said primary stream over the entire inlet area of said column.

9. The device as defined by claim 8, further comprising a sealing gasket interposed between adjacent blocks.

10. The device as defined by claim 9, said sealing gasket being made of polytetrafluoroethylene.

* * * * *